United States Patent [19]
French et al.

[11] Patent Number: 5,190,168
[45] Date of Patent: Mar. 2, 1993

[54] RACK FOR STORING AND DISPENSING DENTAL TRAYS, AND DENTAL TRAYS FOR USE THEREWITH

[75] Inventors: Leonard French; Marc Gottlieb, both of Commack, N.Y.

[73] Assignee: Affordable Dental Products, East Farmingdale, N.Y.

[21] Appl. No.: 625,819

[22] Filed: Dec. 11, 1990

[51] Int. Cl.⁵ ............................................. A61C 19/00
[52] U.S. Cl. .................................... 211/59.2; 211/13; 312/42; 433/77
[58] Field of Search .................... 211/13, 14, 15, 59.2; 312/42; 433/37, 77; 206/63.5, 369; 221/255, 309, 310, 281

[56] References Cited
U.S. PATENT DOCUMENTS

| | | | |
|---|---|---|---|
| 917,864 | 4/1909 | Hildenbrand | 211/59.2 X |
| 2,147,086 | 2/1939 | Bryan | 211/59.2 X |
| 2,281,208 | 4/1942 | Schwarzkopf | 312/42 |
| 2,555,102 | 5/1951 | Anderson | 206/202 |
| 3,037,638 | 6/1962 | Nealy | 211/59.2 |
| 3,206,067 | 9/1965 | Smith, Jr. et al. | 221/309 X |
| 4,082,209 | 4/1978 | Sanders | 211/15 X |
| 4,140,244 | 2/1979 | Clabby | 312/42 X |
| 4,305,512 | 12/1981 | Mackenzie | 211/59.2 X |
| 4,432,451 | 2/1984 | Hooser | 312/42 X |
| 4,600,251 | 7/1986 | Zimmerman | 312/209 |
| 4,763,791 | 8/1988 | Halverson | 206/570 |

*Primary Examiner*—Carl D. Friedman
*Assistant Examiner*—Derek J. Berger
*Attorney, Agent, or Firm*—Cohen, Pontani, Lieberman, Pavane

[57] ABSTRACT

A refillable rack (10) for storing and dispensing a plurality of items, particularly dental trays (12), has one or more vertical slots (30) in a front wall (28). The defining edges of each slot (30) slidably engage vertical grooves (72) in the dental trays (12) such that a plurality of dental trays may be stacked in each slot. In a preferred embodiment, a movable member (76) at the bottom of each slot is biased to a first position wherein the width of the bottom of the slot (30) is narrower than the spacing between the grooves (72) for retaining the dental trays in the slot, and a second position wherein the width of the bottom of the slot (30) is equal to or greater than the spacing between the grooves (72) such that the lowermost dental tray (12) may be removed from the bottom of the slot, the movable member (76) preferably being movable to its second position by gripping the handle of the lowermost dental tray and moving it downward in the slot against the member for urging it to its second position. Once the lowermost tray is removed, the trays (12) stacked thereabove slide downward in the slot (30) under the influence of gravity and additional trays may be feed into the top of the slot for refilling the rack (10). An improved item (12) for cooperating with a rack (10) of the above-mentioned type is also disclosed.

17 Claims, 3 Drawing Sheets

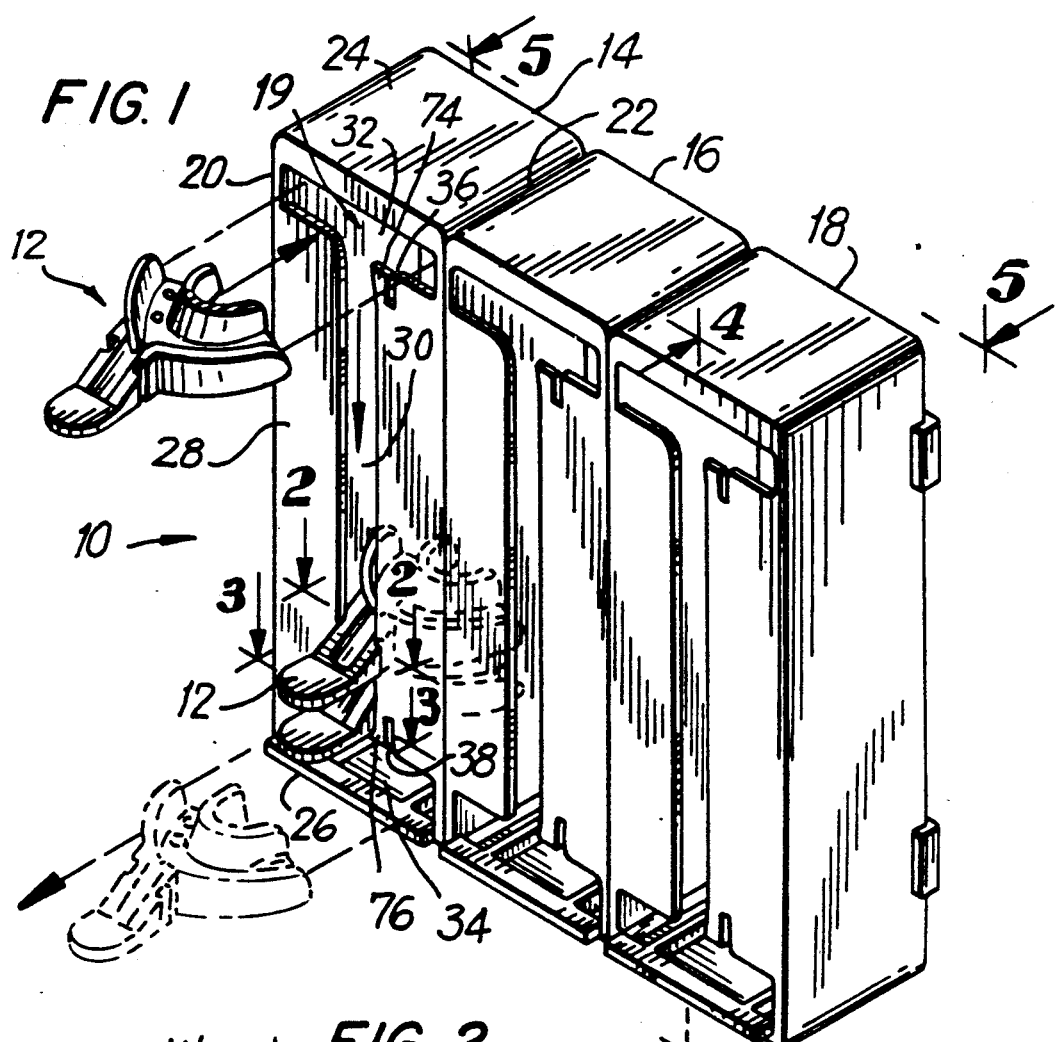
FIG. 1
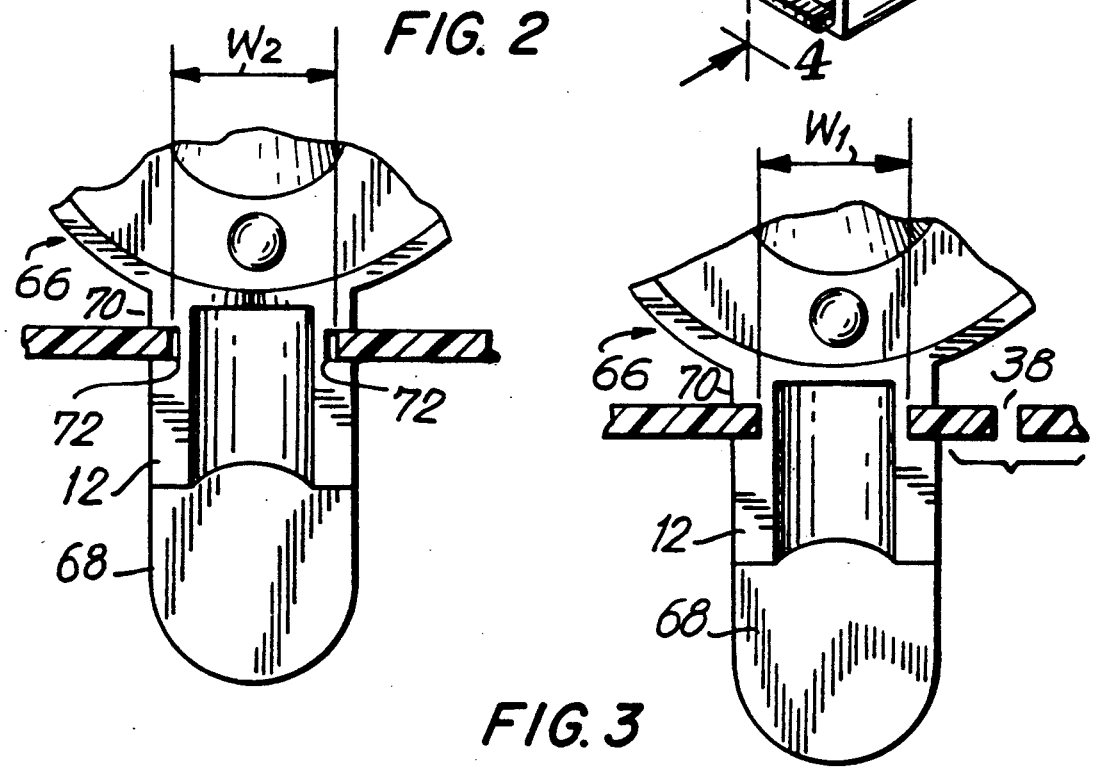
FIG. 2
FIG. 3

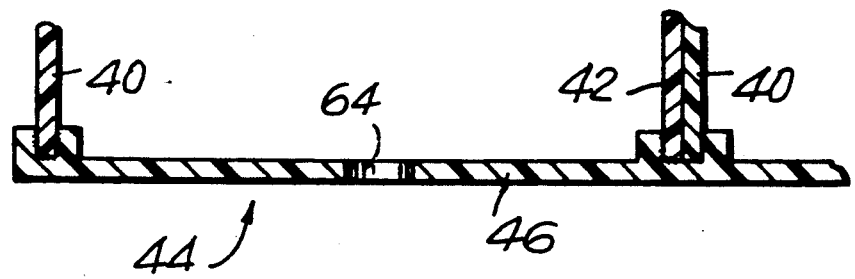
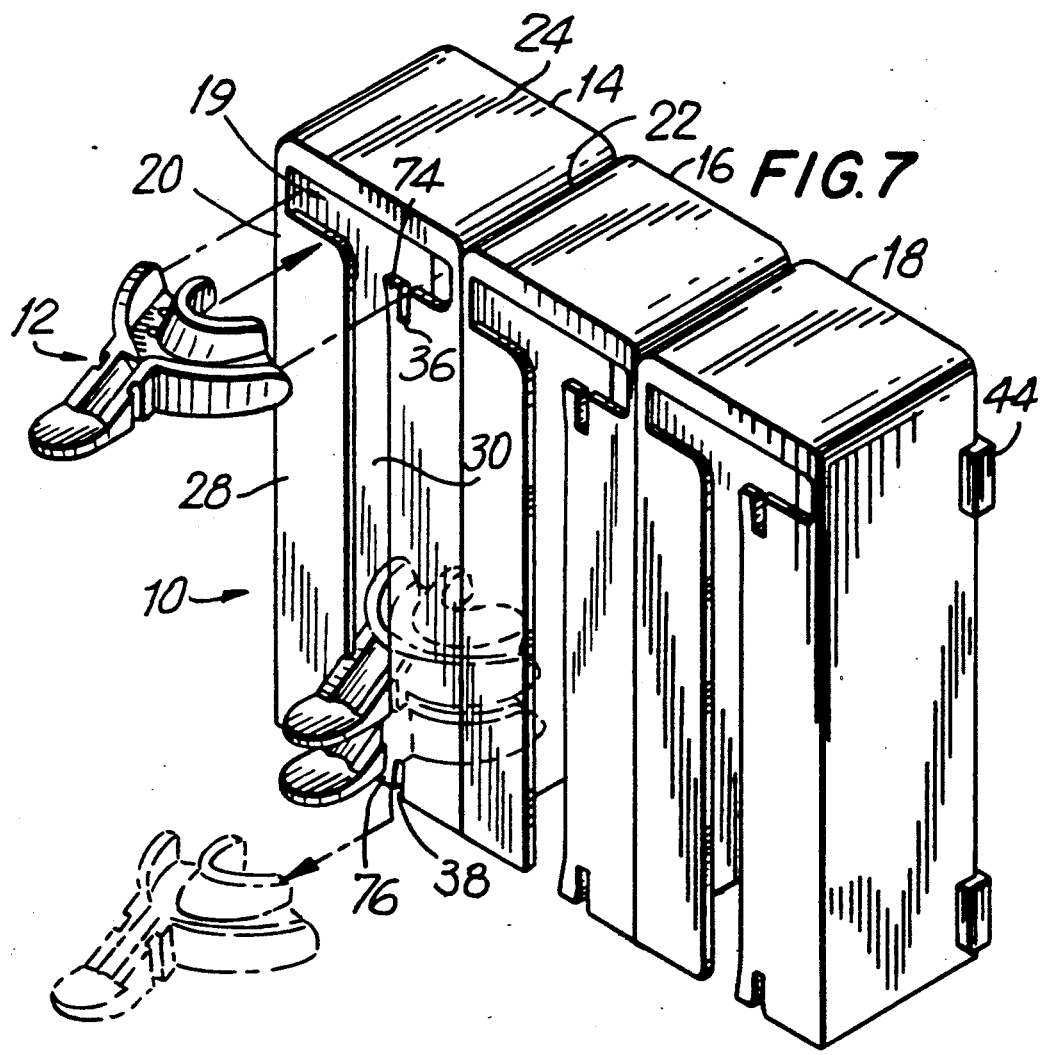

RACK FOR STORING AND DISPENSING DENTAL TRAYS, AND DENTAL TRAYS FOR USE THEREWITH

BACKGROUND OF THE INVENTION

1. Field of the Invention

This invention pertains to racks for storing and dispensing a plurality of items, particularly dental trays.

2. Prior Art

Certain medical items are frequently used, and it desirable to store such items in a manner which facilitates dispensing. For example, where the items are dental trays for making dental impressions, it is desirable to have a rack for storing the trays when not in use, yet which conveniently dispenses them when needed. The rack should also be easy to fill as the dental trays therein are depleted.

While the prior art discloses various racks and the like for storing a plurality of items, the prior art does not teach or suggest a rack having the aforementioned properties. For example, Zimmerman, U.S. Pat. No. 4,600,251, discloses a rack for supporting a plurality of dental trays by their respective handles. The rack, however, is only designed to hold the trays as the impressionable material therein sets, and is not designed or intended for storing and dispensing the trays prior to use.

Haverson, U.S. Pat. No. 4,763,791, discloses a dental impression kit comprising a plurality of dental trays stored in a support member comprising a filler material, such as expanded foam. It will be immediately apparent, however, that this approach to storing dental trays is not space efficient. Rather, the appeal of this device is its portability.

Therefore, it is an object of the present invention to provide a rack for conveniently storing unused dental trays and dispensing them as needed.

It is a further object of the present invention to provide a rack of the aforementioned type which is also easily refillable as the dental trays therein are depleted.

It is yet a further object of the present invention to provide a dental tray specifically configured to cooperate with a rack of the aforementioned type.

SUMMARY OF THE INVENTION

Broadly speaking, the present invention comprises a rack for storing and dispensing a plurality of items, particularly dental trays, each item having a pair of grooves on an intermediate section thereof, the grooves having a predetermined width and being separated from each other by a predetermined distance, the rack comprising: a first compartment defining a space for receiving the items, the compartment including a front wall having a vertically extending slot therein in communication with the space, the thickness of the front wall defining the slot being less than the predetermined width of the grooves and the spacing between the defining walls of the slot being dimensioned for a sliding fit in said pair of grooves for securing the items in the compartment with a first portion of the items in the space and a second portion thereof outside the space, with an item being slidably movable in the slot by gripping the second portion thereof; and means disposed at the bottom of the slot for retaining the items therein against downward sliding movement, the means comprising a first member constricting the width of the slot at the bottom thereof to less than the predetermined distance between the grooves.

In a preferred embodiment, the portion of the front wall adjacent the lower end of the slot has a slit therein and the first member comprises the portion of the front wall between the vertical slot and the slit, the first member being biased to a first position wherein the width of the slot at the bottom thereof is less than the predetermined distance between the grooves, and a second position wherein the width of the slot at the bottom thereof is greater than the predetermined distance between the grooves such that the lowermost item in the slot may be extracted from the slot, the member being movable to the second position by gripping the second portion of the item and pulling it downward in the slot against the movable member. Where a single storage compartment is not sufficient, a plurality of identical compartments may be joined in tandem.

In a most preferred embodiment, the compartment also comprises top and bottom walls spaced from the top and bottom of the vertical slot for defining, respectively, top and bottom openings in communication with the slot, the height of the top and bottom openings being greater than the height of the items whereby the items may be inserted through the top opening for feeding into the slot and extracted from the compartment through the bottom opening.

As will be apparent from the foregoing, the rack in accordance with the present invention is capable of conveniently and inexpensively storing a plurality of dental trays stacked one on top of the other in the vertical slot, with the lowermost dental tray being removable from the bottom of the slot when the movable member is in its second position. Preferably, the slots are refilled by inserting additional dental trays in the top of the slot as the supply therein is depleted. Means are also preferably provided for securing the compartment to a vertical surface, such as a wall in a dental office.

The present invention is also for an item for use with a storage and dispensing rack of the type comprising: a first compartment defining a space for receiving the item, the compartment including a front wall having a vertically extending slot of predetermined width in communication with the space; and a first member constricting the width of the slot at the bottom thereof to less than the predetermined width; the item being of the type having a first, operative portion, a second portion for gripping the item, and an intermediate section joining the first and second portions the improvement comprising the intermediate section of the item having a pair of grooves therein separated by a predetermined distance which is less than the predetermined width of the slot but greater than the width of the slot when constricted by the first member, each groove having a predetermined width which is greater than the thickness of the front wall defining the slot whereby the item may be slidably received in the slot when the defining walls of the slot are received in the grooves for securing the item in the compartment with the first portion thereof in the space and the second portion thereof outside the space, with the first member restricting downward sliding movement of the item in the slot. In a preferred embodiment, the item comprises a dental tray, the intermediate section thereof is thickened, and the groove extend the full thickness of the intermediate section.

The foregoing as well as additional features and advantages of the dental tray in accordance with the present invention will be more fully apparent from the fol-

BRIEF DESCRIPTION OF THE DRAWINGS

In the drawings:

FIG. 1 is a perspective view of a rack for storing and dispensing dental trays in accordance with the present invention;

FIG. 2 is a sectional view taken substantially along the lines 2—2 in FIG. 1;

FIG. 3 is a sectional view taken substantially along the lines 3—3 in FIG. 1;

FIG. 6 is a sectional view taken substantially along the lines 6—6 in 5; and

FIG. 7 is a perspective view of a modified embodiment of a rack for storing and dispensing dental trays in accordance with the present invention.

DETAILED DESCRIPTION OF THE PREFERRED EMBODIMENT

Figure 4:
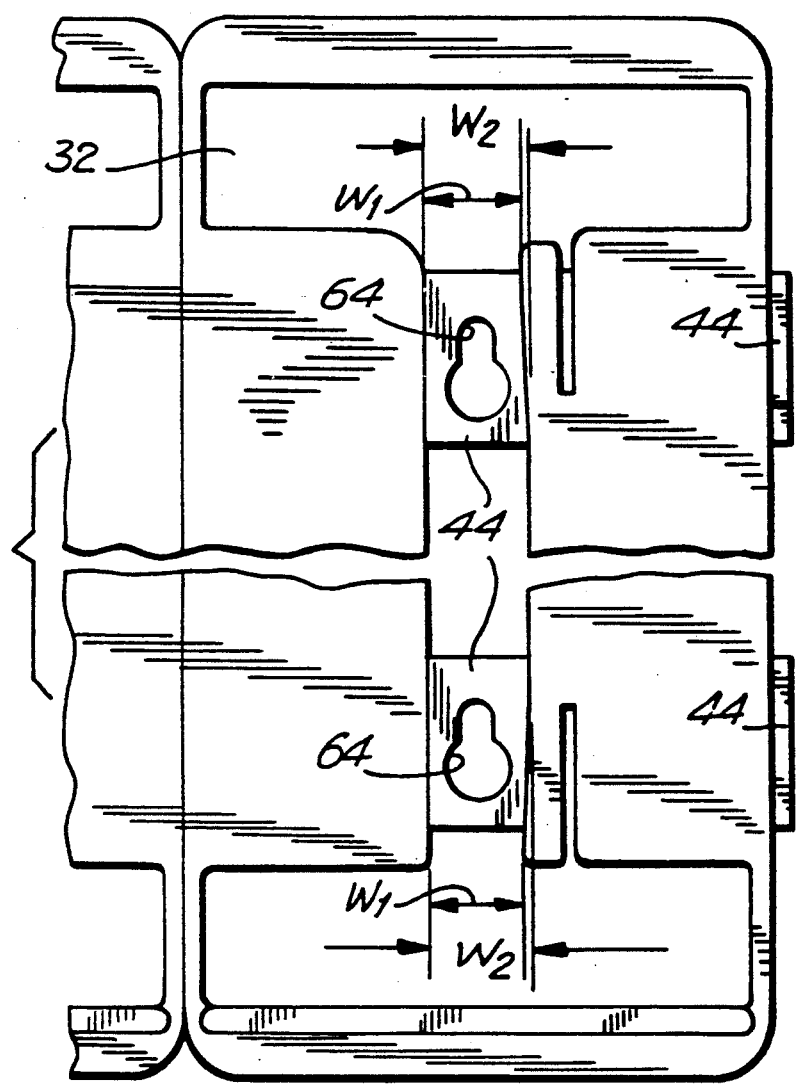
FIG. 4 is a front elevational view of one compartment taken substantially along the lines 4—4 in FIG. 1.
Figure 5:
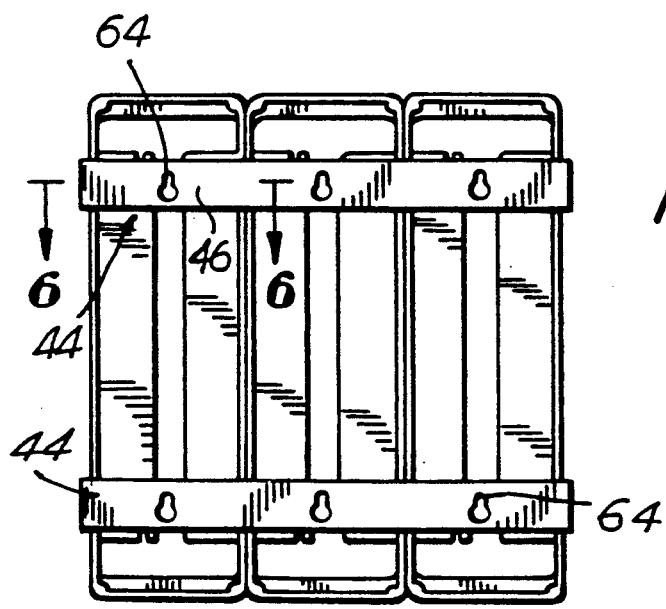
FIG. 5 is a rear elevational view of the rack shown in FIG. 1.

Referring now to the drawings, and initially to FIG. 1 thereof, a preferred rack for storing and dispensing dental trays 12 in accordance with the present invention is generally designated at 10. As shown, the rack 10 comprises three separate, identical compartments 14, 16 and 18 each defining an interior space 19, though as this description progresses it will be apparent that any number of compartments may be incorporated in the rack 10.

Referring now to FIG. 1, the compartment 14 will now be described, it being understood that the construction of the other two compartments 16, 18 is the same. As shown, compartment 14 comprises a box-shaped structure having sidewalls 20, 22, top and bottom walls 24 and 26, respectively, and a front wall 28. The front wall 28 has a vertical slot 30 in communication with top and bottom openings 32 and 34, respectively, and vertically extending top and bottom slits 36 and 38, respectively, adjacent the vertical slot 30. As shown, the back of the compartment 14 is preferably open.

Referring now to FIG. 6, tabs 40, 42 protrude beyond the back of the compartment 14 from the sidewalls 22 and 20, respectively. As will now be explained, these tabs facilitate joining a plurality of compartments 14, 16 and 18 together for creating multicompartment racks, such as the rack 10 shown in FIG. 1. Still referring to FIG. 6, compartments 14, 16 and 18 are joined together by two members 44, each comprising an elongate strip 46 having spaced protrusions 48 defining grooves 56. The outermost grooves 56 are dimensioned for a snap or friction fit about a single tab 40 or 42, whereas the other grooves are dimensioned for a snap or friction fit about two adjacent tabs 40, 42. Thus, and as best shown in FIGS. 1 and 6, when the compartments 14, 16 and 18 are placed side-by-side, the grooves in the members 44 may be snapped fit over the tabs 40, 42 for securing the compartments 14, 16 and 18 together for defining a single, multi-compartment rack 10. To insure securement of the tabs 40, 42 in the grooves 56 an adhesive may also be employed. As shown, the members 44 are provided with spaced keyhole shaped openings 64 for supporting the rack on a wall or other vertical surface in a manner well known to those of ordinary skill in the art. Preferably, the compartments 14, 16, 18 and the members 44 are injection molded from plastic, such as polystyrene.

Referring now to FIG. 2, a dental tray 12 usable with the rack 10 is shown. In large part, the dental tray 12 is conventional, incorporating both a section 66 for receiving the impressionable polyiaestic material from which the dental impression is made and a handle 68 for gripping the tray 12. However, unlike conventional dental trays, the intermediate section 70 joining the handle 68 to the section 66 is thickened and the thickened section 70 has a pair of vertically extending grooves 72 on either side thereof. As will be more fully described below, these grooves 72 cooperate with the defining walls of the slots 30 in the compartments 14, 16, 18.

In use, the rack 10 will be secured to a wall or other vertical surface by screws or the like extending through the keyholes 64 in the members 44. To this end, each rack 10 may be provided with a paper or cardboard template to facilitate registration of the screwholes on the vertical surface, all in a manner well known in the art. Once the rack is secured, the slots 30 are filled with a plurality of unused dental trays 12. To insert a tray 12 into a slot 30, the tray is fed through the opening 32 until its grooves 72 are aligned with the defining edges of the corresponding slot 30, whereupon the tray may be pulled down into the slot by its handle 68. Unused dental trays are repeatedly inserted through the openings 32 into the slots 30 in the above-described manner, preferably until each slot 30 is filled with dental trays. For example, the height of each slot 30 may be dimensioned to receive up to eleven unused dental trays. Of course, to this end, the height of each opening 32 is somewhat greater than the height of a tray 12.

As preferred and shown, the slot 30 is somewhat narrowed at its upper and lower ends adjacent the slits 36, 38. In particular, the width $W_1$ of the slot 30 at these locations is slightly less than the width of the section 70 between the grooves 72. Consequently, as each tray 12 is fed into a slot 30, the arm 74 defined between the slit 36 and slot 30 must be flexed toward the slit 36 to widen the upper end of the slot 30. On the other hand, the width $W_2$ of the central portion of the slot 30 between the slits 36, 38 is slightly wider than the spacing between the grooves 72 such that once a tray 12 is forced beyond the arm 74, it freely slides in the slot 30 to the bottom thereof under the influence of gravity until it reaches the narrowed portion of the slot 30 adjacent the arm 76. At this point, the tray 12 is precluded from further sliding downward movement since the width of a slot 30 at this location is again slightly narrower than the spacing between the grooves 72 on the dental tray 12.

As should by now be apparent, to remove a dental tray 12 from the rack 10, the user grips the handle 68 of the lowermost tray in one of the slots 30. Pulling down on the lowermost tray 12 urges the arm 76 toward the slit 38 thereby allowing the lowermost tray 12 to pass into the opening 34 from which it can be extracted from the rack 10. As this is done, the dental trays 12 thereabove slide down the slot 30 under the influence of gravity, with the new lowermost tray retained in the slot 30 by virtue of the narrowing at the bottom thereof. It will be apparent that as the supply of dental trays 12 in the rack 10 is depleted, the rack 10 may be refilled by simply inserting additional dental trays 12 through the openings 32 and into the slots 30 in the manner described above.

From the foregoing it will be apparent that the rack 10 is well suited to its intended purpose of storing and dispensing dental trays 12 as and when needed. Moreover, the ability to place a plurality of compartments, such as compartments 14, 16 and 18, in tandem accommodates use in dental offices of varying sizes. In this regard, while the members 44 are specifically designed for joining three compartments, that is not mandatory, and members 44 adapted for securing two or more than three compartments are feasible. In the event a single compartment is used, the members 44 are still desirable as they provide the keyholes 64 for securing the compartment to a vertical surface. Of course, once this description is known, persons of ordinary skill in the art will undoubtedly perceive yet additional ways for securing one or more such compartments to a vertical surface.

As shown in FIG. 7, if desired, the bottom walls 26 of the compartments 14, 16, 18 may be eliminated along with the portions of the sidewalls 20, 22 defining the bottom openings 32. Similarly, the top walls 24 and the portions of the sidewalls 20, 22 defining the top openings 32 may also be eliminated. However, this latter modification is not preferred, as it would expose the uppermost tray 12 in each compartment 14, 16, 18, to dust and other airborne contaminants. As a yet further possibility, each slot 30 may be closed at the bottom thereof, such that the dental trays 12 may only be inserted and removed through the top of the slots 30. dental trays 12 in each slot 30 may not be used for some time if the slots 30 are routinely refilled before all the trays therein are used. It will also be apparent from the foregoing description that the upper slit 36 and the narrowed portion of the slot 30 adjacent thereto are not mandatory, and that such may be dispensed with.

Since the foregoing as well as further changes and modifications will be apparent to persons of ordinary skill in the art who have read this description, the above description should be construed as illustrative, and not in a limiting sense, the scope of the invention being defined by the following claims.

We claim:

1. A rack for storing and dispensing a plurality of items, particularly dental trays, each item having a pair of grooves on an intermediate section thereof, the grooves having a predetermined width and being separated from each other by a predetermined distance, said rack comprising:

a first compartment defining a space for receiving the items, said compartment including a front wall having a vertically extending slot therein in communication with said space, said vertically extending slot having a pair of defining walls, the thickness of said front wall defining said slot being less than the predetermined width of the grooves of the item and the distance between said pair of defining walls of said slot being dimensioned for a sliding fit in the pair of grooves for securing the items in said compartment with a first portion of the items said space and a second portion thereof outside said space, the item being slidably movable in said slot by gripping the second portion thereof; and means disposed at the bottom of said slot for retaining the items therein against downward sliding movement, said means comprising a first member constricting the width of said slot at the bottom thereof to less than said predetermined distance between the grooves, wherein said first member is movable between a first position and a second position and comprises a member movable between said first position wherein the width of said slot at the bottom thereof is less than said predetermined distance and said second position wherein the width of said slot at the bottom thereof is equal to or greater than said predetermined distance, whereby the lowermost dental tray in said slot may be removed from the bottom thereof only when said first member is in said second position.

2. The rack of claim 1, wherein said rack is comprised of plastic, said front wall of said compartment further comprises a first slit adjacent the lower end of said slot on one side thereof, and said first member comprises a portion of said front wall defined between said vertical slot and said first slit, said member being biased to its first position by a memory of said plastic and movable to said second position under an urging of a lowermost item as it is slid downward in said slot against said first member.

3. The rack of claim 2, wherein said compartment further comprises a top wall spaced from the top of said vertical slot for defining a top opening in communication with said slot, the height of said top opening being greater than the height of the items whereby the items may be passed through said top opening for feeding into said slot.

4. The rack of claim 3, wherein said compartment further comprises a bottom wall spaced from the bottom of said vertical slot for defining a bottom opening in communication with said slot, the height of said bottom opening being greater than the height of the items whereby the items may be moved from said slot into said bottom opening for extraction from said compartment.

5. The rack of claim 3, wherein said compartment further comprises a second member at the upper end of said vertical slot biased to a first position by the memory of said plastic wherein the width of said upper end of said vertical slot is less than said predetermined distance, said second member being movable to a second position wherein the width of the upper end of said vertical slot is equal to or greater than said predetermined distance whereby the items may be inserted in the upper end of said vertical slot only when said member is in said second position, said second member being movable to said second position by the urging of the item against said second member.

6. The dental tray of claim 5, wherein said front wall has a second slit therein adjacent the upper end of said vertical slot, and wherein said second member comprises the portion of said front wall between said vertical slot and said second slit.

7. The rack of claim 3, further comprising means for securing said compartment to a vertical surface.

8. The rack of claim 3, wherein said rack further comprises a plurality of dental trays, and wherein the first portion of said trays comprises means for receiving an impressionable material and the second portion of said trays comprises means for gripping said trays.

9. The rack of claim 3, further comprising:

a second compartment defining a space for receiving the items, said second compartment including a front wall having a vertically extending slot therein in communication with said space, the thickness of said front wall defining said slot being less than said predetermined width of said grooves and the spacing between the defining walls of said slot being dimensioned for a sliding fit in said pair of grooves for securing the items in said second compartment with a first portion of the items in said space and a second portion thereof outside said space;

means disposed at the bottom of said slot in said second compartment for retaining the items therein against downward sliding movement, said means comprising a first member constricting the width of said slot at the bottom thereof to less than said predetermined distance between said grooves; and means for joining said first and second compartments.

10. The rack of claim 1, wherein said compartment further comprises top and bottom walls spaced from the top and bottom of said vertical slot for defining, respectively, top and bottom openings in communication with said slot, the height of said top and bottom openings being greater than the height of the items whereby the items may be inserted through said top opening for feeding into said slot and extracted from said compartment through said bottom opening.

11. The rack of claim 1, wherein said rack further comprises a plurality of dental trays, and wherein the first portion of said trays comprises means for receiving an impressionable material and the second portion of said trays comprises means for gripping said trays.

12. The rack of claim 1, further comprising:

a second compartment defining a space for receiving the items, said second compartment including a front wall having a vertically extending slot therein in communication with said space, the thickness of said front wall defining said slot being less than the predetermined width of said grooves and the spacing between the defining walls of said slot being dimensioned for a sliding fit in said pair of grooves for securing the items in said second compartment with a first portion of the items in said space and a second portion thereof outside said space;

means disposed at the bottom of said slot in said second compartment for retaining the items therein against downward sliding movement, said means comprising a first member constricting the width of said slot at the bottom thereof to less than said predetermined distance between said grooves; and means for joining said first and second compartments.

13. In an item for use with a storage and dispensing rack, the rack comprising a first compartment defining a space for receiving the item, said compartment including a front wall having a vertically extending slot of predetermined width therein in communication with said space, and a first member constricting the width of said slot at the bottom thereof to less than said predetermined width, the item being of the type having a first, operative portion, a second portion for gripping the item, and an intermediate section joining said first and second portions, the improvement comprising:

said intermediate section having a pair of grooves therein separated by a predetermined distance which is less than said predetermined width of said slot but greater than the width of said slot when constricted by said first member, each groove having a predetermined width which is greater than the thickness of said front wall defining said slot and the width of said first and second positions being greater than the width of said slot, whereby the item may be slidably received in said slot when the defining walls of said slot are received in said grooves for securing the item in said compartment with said first portion thereof in said space and said second portion thereof outside said space, said first member restricting downward sliding movement of the item in said slot.

14. The item of claim 13, wherein the item comprises a dental tray and wherein said second portion of said dental tray comprises the handle thereof.

15. The item of claim 14, wherein said intermediate section has a thickened region and wherein said grooves extend the full length of said thickened region of said intermediate section.

16. The item of claim 15, wherein said dental tray and the rack are comprised of plastic.

17. The item of claim 14, wherein said dental tray and the rack are comprised of plastic.

* * * * *